United States Patent
Amemiya (10) Patent No.: US 7,111,515 B2
(45) Date of Patent: Sep. 26, 2006

(54) ULTRASONIC DIAGNOSTIC APPARATUS AND DRIVING METHOD THEREFOR

(75) Inventor: Shinichi Amemiya, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 143 days.

(21) Appl. No.: 11/009,507

(22) Filed: Dec. 10, 2004

(65) Prior Publication Data

US 2005/0126292 A1 Jun. 16, 2005

(30) Foreign Application Priority Data

Dec. 11, 2003 (JP) .............................. 2003-413163

(51) Int. Cl.
*G01N 29/06* (2006.01)
*A61B 8/00* (2006.01)

(52) U.S. Cl. ........................... 73/602; 73/826; 600/447

(58) Field of Classification Search ................. 73/602, 73/626; 600/447
See application file for complete search history.

(56) References Cited

U.S. PATENT DOCUMENTS

| | | | |
|---|---|---|---|
| 3,676,839 A | 7/1972 | Wohl et al. | |
| 4,204,435 A | 5/1980 | Bridoux et al. | |
| 4,241,608 A * | 12/1980 | Dees et al. .................... | 73/606 |
| 4,463,763 A | 8/1984 | Koyano et al. | |
| 4,817,616 A | 4/1989 | Goldstein | |
| 5,211,059 A | 5/1993 | Hayakawa | |
| 5,343,864 A | 9/1994 | Sugiyama | |
| 5,379,642 A * | 1/1995 | Reckwerdt et al. ........... | 73/625 |
| 5,520,186 A | 5/1996 | Deitrich | |
| 6,183,419 B1 * | 2/2001 | Wildes ....................... | 600/447 |
| 6,248,072 B1 | 6/2001 | Murkin | |
| 6,352,508 B1 * | 3/2002 | Pang et al. ................. | 600/443 |
| 6,476,541 B1 | 11/2002 | Smith et al. | |
| 6,659,949 B1 * | 12/2003 | Lang et al. ................. | 600/438 |
| 6,705,997 B1 | 3/2004 | Amemiya | |

FOREIGN PATENT DOCUMENTS

JP 2003-260055 9/2003

* cited by examiner

*Primary Examiner*—Daniel S. Larkin
*Assistant Examiner*—Rose M. Miller
(74) *Attorney, Agent, or Firm*—Carl B. Horton, Esq.; Armstrong Teasdale LLP (57) ABSTRACT

An ultrasonic diagnostic apparatus for transmitting ultrasonic signals toward a subject, receiving signals reflected from the subject in response to the transmitted ultrasonic signals, and producing a tomographic image of the subject based on the received signals, includes: transmitting/receiving device having a plurality of channels for transmitting/receiving ultrasonic signals via the channels; and a linear or convex probe in which transducers in a number larger than the number of channels are arranged in one direction, in which probe, the transducers are connected to the channels inconsecutively in the arrangement direction, and the number of transducers in an aperture area from one end to the other of transducers that are connected to the channels is set to be larger than the number of channels.

13 Claims, 10 Drawing Sheets

Ultrasonic probe 2

| | e0 | e1 | e2 | e3 | e4 | e5 | e6 | e7 | e8 | e9 | e10 | e11 | e12 | e13 | e14 | e15 |
|---|---|---|---|---|---|---|---|---|---|---|---|---|---|---|---|---|
| 1st | 0 | 0 | 0 | 1 | 0 | 1 | 0 | 1 | 1 | 1 | 1 | 0 | 1 | 0 | 1 | 0 |
| 2nd | 0 | 0 | 1 | 0 | 1 | 0 | 1 | 1 | 1 | 1 | 0 | 1 | 0 | 1 | 0 | 0 |
| 3rd | 0 | 1 | 0 | 1 | 0 | 1 | 1 | 1 | 1 | 0 | 1 | 0 | 1 | 0 | 0 | 0 |
| 4th | 1 | 0 | 1 | 0 | 1 | 1 | 1 | 0 | 0 | 1 | 0 | 1 | 0 | 0 | 0 | 0 |
| 5th | 0 | 1 | 0 | 1 | 1 | 1 | 0 | 1 | 1 | 0 | 1 | 0 | 0 | 0 | 0 | 0 |
| 6th | 1 | 0 | 1 | 1 | 1 | 1 | 1 | 0 | 0 | 1 | 0 | 0 | 0 | 0 | 0 | 0 |
| 7th | 0 | 1 | 1 | 1 | 0 | 0 | 0 | 1 | 1 | 0 | 0 | 0 | 0 | 0 | 0 | 0 |
| 8th | 1 | 1 | 1 | 1 | 0 | 1 | 0 | 0 | 0 | 0 | 0 | 0 | 0 | 0 | 0 | 0 |
| 9th | 1 | 1 | 1 | 1 | 0 | 1 | 0 | 1 | 0 | 0 | 0 | 0 | 0 | 0 | 0 | 0 |
| 10th | 1 | 1 | 1 | 1 | 0 | 1 | 0 | 1 | 0 | 0 | 0 | 0 | 0 | 0 | 0 | 0 |

| | Row 1 | Row 2 | Row 3 |
|---|---|---|---|
| | 0 | 0 | 0 |
| | 0 | 0 | 0 |
| | 0 | 0 | 0 |
| | 0 | 1 | 0 |
| | 0 | 0 | 1 |
| | 1 | 1 | 0 |
| | 0 | 0 | 1 |
| | 1 | 1 | 1 |
| Ultrasonic probe 2 | 1 | 1 | 1 |
| | 1 | 1 | 1 |
| | 1 | 1 | 0 |
| | 0 | 0 | 1 |
| | 1 | 1 | 0 |
| | 0 | 0 | 1 |
| | 0 | 1 | 1 |
| | 0 | 0 | 0 |

ULTRASONIC DIAGNOSTIC APPARATUS AND DRIVING METHOD THEREFOR

CROSS REFERENCE TO RELATED APPLICATIONS

This application claims the benefit of Japanese Application No. 2003-413163 filed Dec. 11, 2003.

BACKGROUND OF THE INVENTION

The present invention relates to an ultrasonic diagnostic apparatus and a driving method therefor, and particularly to an ultrasonic diagnostic apparatus comprising a probe having a larger number of transducers than the number of channels in transmitting/receiving means, and a driving method for such an apparatus.

Apparatuses for scanning a predefined region in a subject to be imaged by ultrasound to produce an image of the subject include the ultrasonic diagnostic apparatus. The ultrasonic diagnostic apparatus is attracting attention because it can conduct a scan and produce an image without distressing the subject to be imaged.

The image produced by the ultrasonic diagnostic apparatus depends considerably upon the number of transmitting/receiving channels in the main body of the apparatus and the number of transducers in the probe. That is, the number of transmitting/receiving channels and the number of transducers are set to correspond to each other, and as the width of transducers becomes smaller and the number of transducers becomes larger, the density of scan lines increases, thus improving accuracy of the produced image. The transducers will be sometimes referred to as elements hereinbelow.

There have been developed probes of a linear or convex type that have elements arranged in a one-dimensional manner and have a large number of elements. On the contrary, in a transmitting/receiving circuit having channels for transmitting/receiving ultrasonic signals to/from the elements, the number of channels cannot easily be increased owing to limitation on the size etc. of the ultrasonic diagnostic apparatus. Therefore, a probe with 128–192 elements has been developed for a transmitting/receiving circuit with 32 or 48 channels, for example. In the ultrasonic diagnostic apparatus having such a probe, adjoining elements are connected to respective transmitting/receiving channels, and a linear or convex scan is achieved by sequentially moving the elements driven by the transmitting/receiving channels (see Non-Patent Document 1, for example).

In B-mode compounding in the linear or convex scan, however, driving consecutive elements as described above, hence narrowing an opening, may result in a broader main beam. Alternatively, driving with elements at certain spacings connected to transmitting/receiving channels to widen the area of the transmitting/receiving elements may result in grating lobes.

On the other hand, an active matrix array (sometimes referred to as AMA hereinbelow) probe in which elements are two-dimensionally arranged has been developed for an ultrasonic diagnostic apparatus having a transmitting/receiving circuit with 128 channels or more, although machines in widespread use generally employ a transmitting/receiving circuit with about 64 channels.

Furthermore, in a portable ultrasonic diagnostic apparatus, there is also a problem that the number of transmitting/receiving channels cannot easily be increased owing to size and/or weight considerations.

[non-Patent Document 1]"Handbook for Medical Ultrasonic Instruments," edited by The Electronic Industries Association of Japan, published by Corona Publishing Co., Ltd., Revised Edition 1 (Jan. 20, 1997), page 94, FIG. 3.59; page 97, FIG. 3.64; and page 102, FIG. 3.76.

SUMMARY OF THE INVENTION

Therefore, an object of the present invention is to provide an ultrasonic diagnostic apparatus that efficiently transmits/receives ultrasonic signals to/from an object to be detected without reducing the signal-noise ratio, thereby improving resolution, and a driving method therefor.

[Means for Solving the Problems]

To attain the aforementioned object, an ultrasonic diagnostic apparatus of the present invention is for transmitting ultrasonic signals toward a subject, receiving signals reflected from the subject in response to the transmitted ultrasonic signals, and producing a tomographic image of the subject based on the received signals, and the apparatus comprises: transmitting/receiving means for transmitting/receiving ultrasonic signals via a plurality of channels; and a linear or convex probe in which transducers in a number larger than the number of channels are arranged in one direction, in which probe, said transducers are connected to said channels inconsecutively with respect to the arrangement direction, and the number of transducers in an aperture area from one end to the other of transducers that are connected to the channels is set to be larger than the number of channels.

According to the ultrasonic diagnostic apparatus of the present invention, in a linear or convex probe, connections between transducers and channels are inconsecutive with respect to the arrangement direction. As a result, the probe has a larger aperture area.

To attain the aforementioned object, an ultrasonic diagnostic apparatus of the present invention is for transmitting ultrasonic signals toward a subject, receiving signals reflected from the subject in response to the transmitted ultrasonic signals, and producing a tomographic image of the subject based on the received signals, and the apparatus comprises: transmitting/receiving means for transmitting/receiving ultrasonic signals via a plurality of channels; and a probe in which transducers in a number larger than the number of channels are arranged in a two-dimensional manner, in which probe, the transducers are connected to the channels inconsecutively with respect to one of the arrangement directions so that a connection pattern of the transducers with the channels in each row is different from that in an adjacent transducer row.

According to the ultrasonic diagnostic apparatus of the present invention, in a probe having transducers arranged in a two-dimensional manner, connections between transducers and channels are organized inconsecutively with respect to one of the arrangement directions. In the other of the arrangement directions, connections between transducers and channels are organized with different connection patterns of transducers with channels. As a result, the probe has a larger aperture area.

To attain the aforementioned object, a driving method of the present invention is for an ultrasonic diagnostic apparatus comprising transmitting/receiving means for transmitting/receiving ultrasonic signals via a plurality of channels, and a linear or convex probe in which transducers connectable to the channels via switches in a number larger than the number of channels are arranged in one direction, and the method comprises the steps of: selecting transducers to be connected to the channels in the transmitting/receiving means, connecting the selected transducers to the channels, transmitting ultrasonic signals toward a subject, and receiving signals reflected in response to the transmitted ultrasonic signals; and producing a tomographic image of the subject based on the received signals, wherein said transmitting/receiving step comprises selecting the transducers to be connected to the channels inconsecutively in the arrangement direction so that the number of transducers in an aperture area from one end to the other of transducers that are connected to the channels is larger than the number of channels.

According to the driving method of the present invention, transducers to be connected to the channels in the transmitting/receiving means are selected, the selected transducers are connected to the channels, ultrasonic signals are transmitted toward a subject, and signals reflected in response to the transmitted ultrasonic signals are received.

At this step, the transducers to be connected to the channels are selected inconsecutively in the arrangement direction so that the number of transducers in an aperture area from one end to the other of transducers that are connected to the channels is larger than the number of channels.

Then, a tomographic image of the subject is produced based on the received signals.

To attain the aforementioned object, a driving method of the present invention is for an ultrasonic diagnostic apparatus comprising transmitting/receiving means for transmitting/receiving ultrasonic signals via a plurality of channels, and a probe in which transducers connectable to the transmitting/receiving means via switches in a number larger than the number of channels are two-dimensionally arranged, and the method comprises the steps of: selecting transducers to be connected to the channels in the transmitting/receiving means, connecting the selected transducers to the channels, transmitting ultrasonic signals toward a subject, and receiving signals reflected in response to the transmitted ultrasonic signals; and producing a tomographic image of the subject based on the received signals, wherein said transmitting/receiving step comprises connecting the transducers to the channels inconsecutively with respect to one of the arrangement directions of the probe, and selecting the transducers so that connection patterns of the channels with the transducers are different between the rows in the probe.

According to the driving method of the present invention, transducers to be connected to the channels in the transmitting/receiving means are selected, the selected transducers are connected to the channels, ultrasonic signals are transmitted toward a subject, and signals reflected in response to the transmitted ultrasonic signals are received.

At this step, the transducers are connected to the channels inconsecutively with respect to one of the arrangement directions of the probe, and the transducers are selected so that connection patterns of the transducers with the channels are different between the rows in the probe.

Then, a tomographic image of the subject is produced based on the received signals.

According to the ultrasonic diagnostic apparatus of the present invention, ultrasonic signals are efficiently transmitted/received to/from an object to be detected without reducing the signal-noise ratio, thereby improving resolution.

According to the driving method of the present invention, ultrasonic signals are efficiently transmitted/received to/from an object to be detected without reducing the signal-noise ratio, thereby improving resolution.

Further objects and advantages of the present invention will be apparent from the following description of the preferred embodiments of the invention as illustrated in the accompanying drawings.

DETAILED DESCRIPTION OF THE INVENTION

The best mode for carrying out the present invention will now be described with reference to the accompanying drawings.

(First Embodiment)

Figure 1:
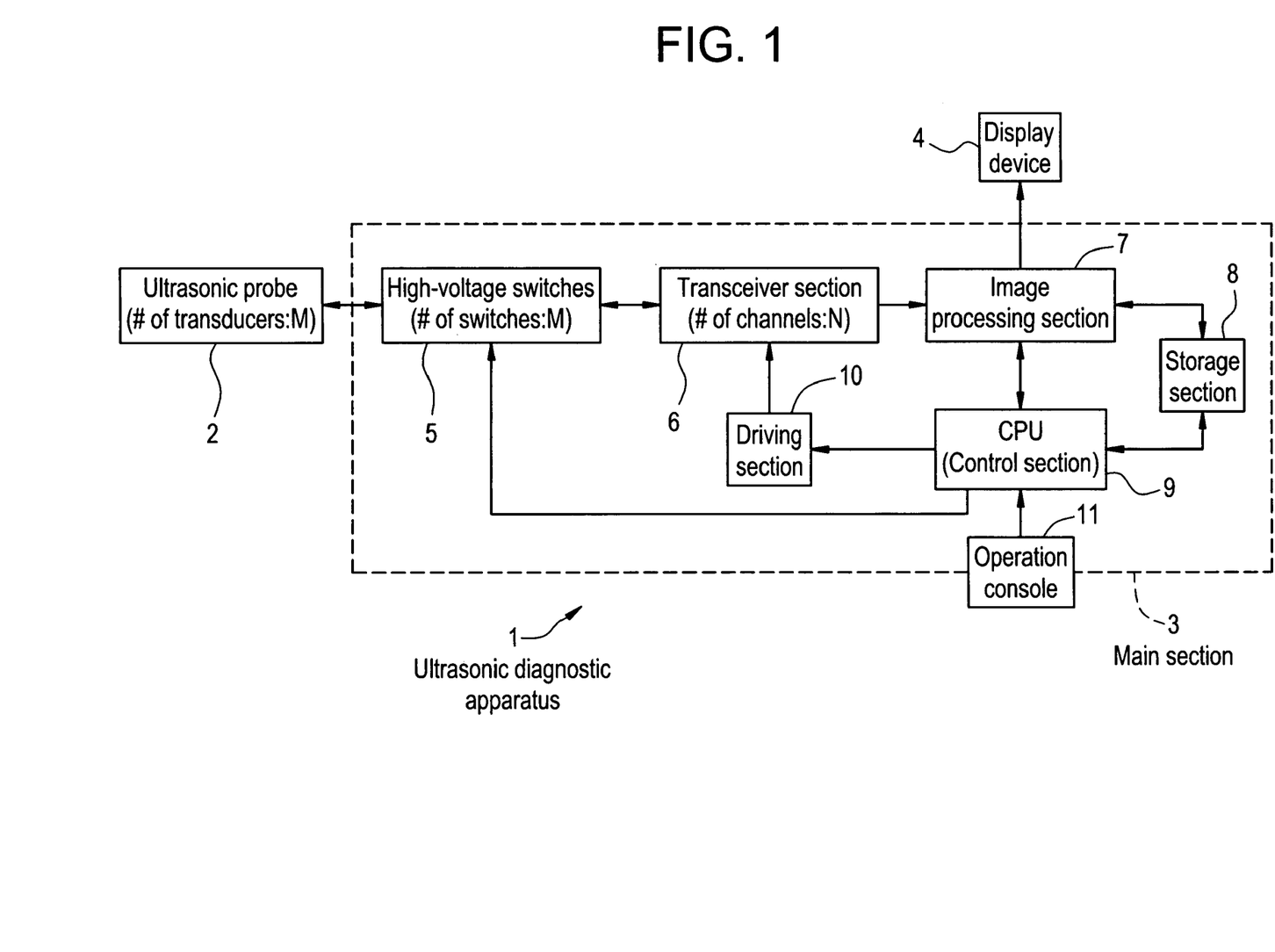
FIG. 1 is a block diagram schematically showing an ultrasonic diagnostic apparatus 1 in accordance with an embodiment of the present invention.

FIG. 1 is a schematic block diagram generally showing an ultrasonic diagnostic apparatus 1 in accordance with the present embodiment.

The ultrasonic diagnostic apparatus 1 in accordance with the present embodiment comprises an ultrasonic probe 2, a main section 3, and a display device 4. The ultrasonic probe 2 and main section 3 are connected to each other via a probe cable, which is not shown.

In ultrasonic imaging, a physician, for example, is the user conducting a scan with the ultrasonic diagnostic apparatus 1. In imaging, the ultrasonic probe 2 is held by the user and is put against the subject.

The ultrasonic probe 2 is connected to a transceiver section 6 via high-voltage switches 5 in the main section 3, which will be described later. The ultrasonic probe 2 has a linear array in which M transducers are arranged in one direction, for example.

The ultrasonic probe 2 converts electric signals supplied from the transceiver section 6 via the high-voltage switches 5 into ultrasound by the transducers and transmits them to the subject. The ultrasonic probe 2 also converts reflected waves from the subject into electric signals by the transducers and outputs them to the transceiver section 6 via the high-voltage switches 5. The ultrasound transmitted by the transducers forming an acoustic line generates echoes corresponding to the difference in acoustic impedance of the internal tissue of the subject during travel inside the subject. These echoes are received by the ultrasonic transducer array and converted into electric signals. As used herein, the term ultrasonic signals refer to both electric signals and ultrasound converted by the transducers.

The ultrasonic probe 2 used in the present embodiment is a linear or convex probe. The ultrasonic probe 2 scans a uniform field of view in a linear scan, or alternatively scans a wide field of view in a convex scan. One embodiment of the probe of the present invention corresponds to the ultrasonic probe 2.

The main section 3 comprises the high-voltage switches 5, the transceiver section 6, an image processing section 7, a storage section 8, a CPU (control section) 9, a driving section 10, and an operation console 11. The main section 3 produces several kinds of ultrasonic images of the subject based on electric signals (echo signals) supplied via the probe cable.

In the present embodiment, the main section 3 produces an image of the subject based on the echo signals, i.e., a B-mode image, for example. The main section 3 will now be described.

The high-voltage switches 5 are connected to the transceiver section 6, ultrasonic probe 2, and control section 9. The high-voltage switches 5 consist of, for example, M number of switches. The high-voltage switches 5 are turned on/off based on instructions from the control section 9 to connect the transceiver section 6 and ultrasonic probe 2. One embodiment of the switches of the present invention corresponds to the high-voltage switches 5.

The transceiver section 6 is connected to the high-voltage switches 5, image processing section 7, and driving section 10. The transceiver section 6 is a port for signal transmission and reception. The transceiver section 6 has, for example, N channels. The number of the channels N is smaller than the number of transducers M in the ultrasonic probe 2. The transceiver section 6 sends driving signals supplied from the driving section 10 for driving the ultrasonic probe 2 to the ultrasonic probe 2 via the probe cable. Moreover, the transceiver section 6 sends echo signals received from the ultrasonic probe 2 via the probe cable to the image processing section 7. One embodiment of the transmitting/receiving means of the present invention corresponds to the transceiver section 6.

The control section 9 is connected to the driving section 10, image processing section 7, storage section 8, and operation console 11.

The control section 9 outputs a command signal for causing the ultrasonic probe 2 to transmit ultrasound for imaging to the driving section 10. The control section 9 also outputs a command signal for displaying a tomographic image etc. according to instructions represented by an operation signal from the operation console 11, to the image processing section 7. Moreover, the control section 9 controls storage of image data in the storage section 8 based on instructions from the operation console 11.

The driving section 10 is implemented using an electric/electronic circuit, for example.

The driving section 10 generates a driving signal for driving the ultrasonic probe 2 to form an acoustic line in response to a command signal from the control section 9, and sends the generated driving signal to the transceiver section 6.

The image processing section 7 produces an image of the subject based on echo signals sent by the transceiver section 6. The image processing section 7 also causes the display device 4 to display the produced image in response to instructions from the control section 9. Moreover, the image processing section 7 sends image data to the storage section 8 for storage. The image processing section 7 is comprised of a program and the like.

The storage section 8 may include several kinds of storage devices such as a semiconductor memory and a hard disk drive.

The storage section 8 stores image data sent from the image processing section 7. The storage section 8 also stores a program for operating the ultrasonic diagnostic apparatus 1, acoustic lines used in the program, and several kinds of parameters such as distance to the subject to be imaged.

The operation console 11 is an apparatus for accepting an operation by the operator for operating the ultrasonic diagnostic apparatus 1. The operation console 11 is comprised of input sections such as a keyboard and switches.

The display device 4 displays an image produced in the main section 3 and other imaging data. The display device 4 is comprised of a CRT or a crystal liquid display panel, for example.

Now an operation of the ultrasonic diagnostic apparatus in accordance with the present invention will be described with reference to the drawings.

Figure 2:
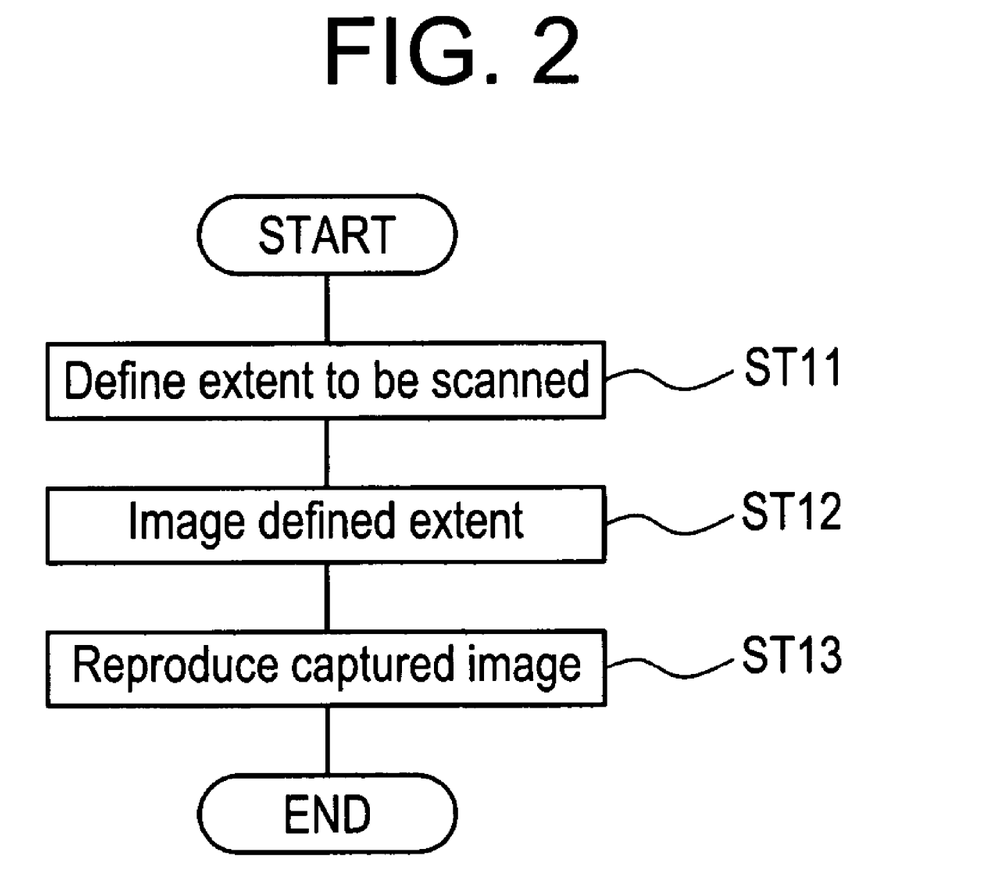
FIG. 2 is a flow chart for explaining an operation of the ultrasonic diagnostic apparatus 1 shown in FIG. 1.

FIG. 2 is a flow chart showing an operation of the ultrasonic diagnostic apparatus 1 in accordance with the present embodiment.

First, an extent to be scanned using the ultrasonic probe 2 is defined (ST11).

The user positions the ultrasonic probe 2 at a certain location of the subject. At that time, depth dimension, azimuthal dimension and thickness dimension of the extent to be scanned are determined depending upon the frequency or scan shape so that the extent to be scanned corresponds to an object to be detected. The extent to be scanned is desirably defined to contain at least the object to be detected.

Next, the region defined at Step ST11 in the subject rested at a predetermined position is imaged (ST12).

The user puts the ultrasonic probe 2 against a scanned position. The user also operates the operation console 11 to supply a command to the driving section 10 via the control section 9. Moreover, the driving section 10, in response to a command signal from the control section 9, generates a driving signal for forming a predetermined acoustic line from combined wavefronts of ultrasound from the ultrasonic transducer array in the ultrasonic probe 2, and outputs it to the ultrasonic probe 2 via the transceiver section 6. The driving section 10 forms a plurality of acoustic lines in one plane (scan plane) in the predefined region, and the ultrasonic probe 2 scans the scan plane by the plurality of acoustic lines. The ultrasonic probe 2 also receives ultrasonic signals coming from the inside of the subject. This step corresponds to one embodiment of the transmitting/receiving step of the present invention.

The step of outputting a signal to the ultrasonic probe 2 at Step ST12 corresponds to the driving method for the ultrasonic diagnostic apparatus of the present invention, details of which will be discussed later.

The transceiver section 6 sends echo signals received by the ultrasonic probe 2 via the probe cable to the image processing section 7.

Based on the echo signals sent from the transceiver section 6 to the image processing section 7, the image processing section 7 conducts what is generally called B-mode processing in which the amplitude of the waveform of echo signals obtained via transmission of acoustic lines is represented as the difference in brightness. The processing provides brightness data in a whole scan plane at resolution corresponding to the number of transmitted acoustic lines. The image processing section 7 produces a two-dimensional image corresponding to the brightness data. This step corresponds to one embodiment of the image producing step of the present invention.

The captured image is stored in the storage section 8 based on instructions by the control section 9.

The captured image stored in the storage section 8 is then reproduced at the display device 4 (ST13).

Figure 3:
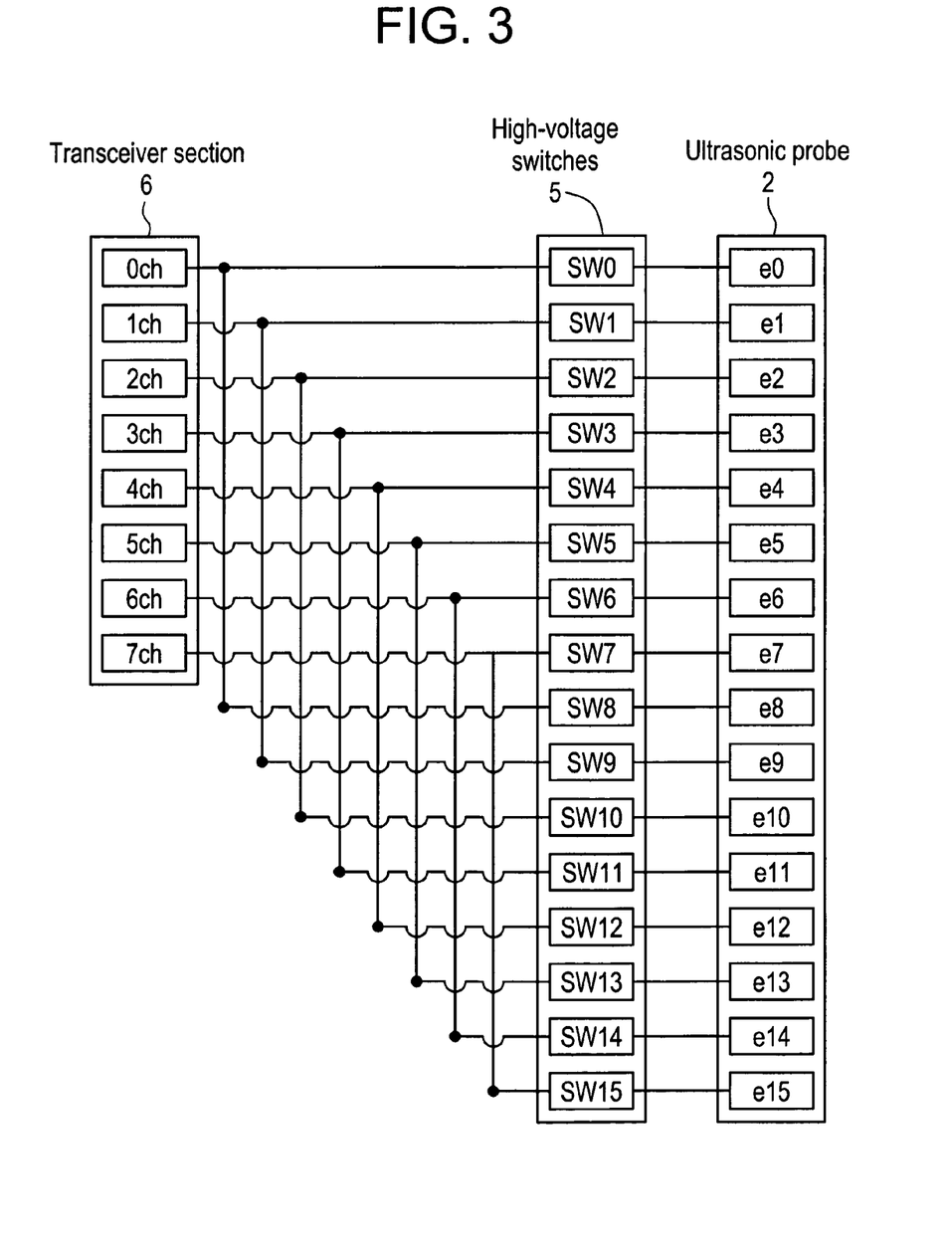
FIG. 3 is a schematic diagram generally showing part of the ultrasonic diagnostic apparatus 1 shown in FIG. 1.

FIG. 3 is an explanatory diagram showing connections between the ultrasonic probe 2, high-voltage switches 5 and transceiver section 6 in accordance with the present invention.

While the number of transmitting/receiving channels in an ultrasonic diagnostic apparatus is generally more than 32, the present embodiment addresses a case in which the number of the channels in the transceiver section 6 is N =8 for simplification. The number of the high-voltage switches 5 and the number of transducers in the ultrasonic probe 2 are M=16 here.

Assuming that N=0–7, an N-th channel is connected to an N-th switch and an (N+8)-th switch in parallel. Moreover, zero-th element e0–$15^{th}$ element e15 in the ultrasonic probe 2 are connected to zero-th switch SW0–$15^{th}$ switch SW15.

At Step ST12, the control section 9 selects elements to be connected to the channels by the high-voltage switches 5, and turns on one of the high-voltage switches 5 to be connected to the channels in the transceiver section 6. At that time, the control section 9 turns on the high-voltage switches 5 so that the elements to be connected to the channels are arranged inconsecutively with respect to the elements' arrangement direction.

This step will now be described in detail with reference to the drawings.

Figure 4:
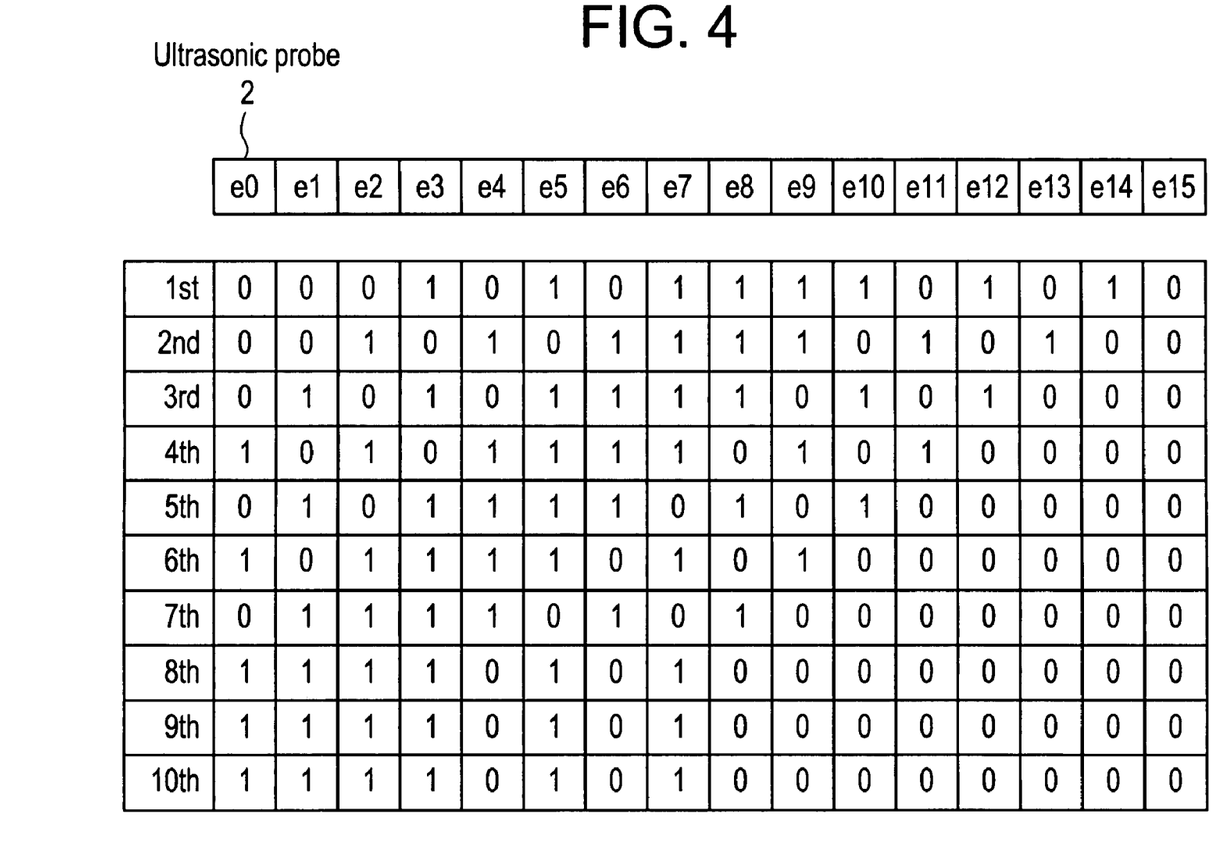
FIG. 4 is a schematic diagram showing an example of a connection pattern of a first embodiment in accordance with the present invention.

FIG. 4 is a schematic diagram generally showing an example of a successive pattern of elements e0–e15 in the ultrasonic probe 2 shown in FIG. 3.

As shown in FIG. 4, based on instructions from the control section 9, first through tenth transmissions/receptions are conducted via the ultrasonic probe 2. Connections between the elements and channels in the transmissions/receptions are indicated by numerals zero and one. Elements e marked with numeral zero have their corresponding high-voltage switches 5 turned off, and those marked with numeral one have their corresponding high-voltage switches 5 turned on. The pattern of arrangement of zero's and one's that indicates connections/disconnections between the elements and channels in the transmissions/receptions will be sometimes referred to as connection pattern of elements with channels hereinbelow.

Figure 5:
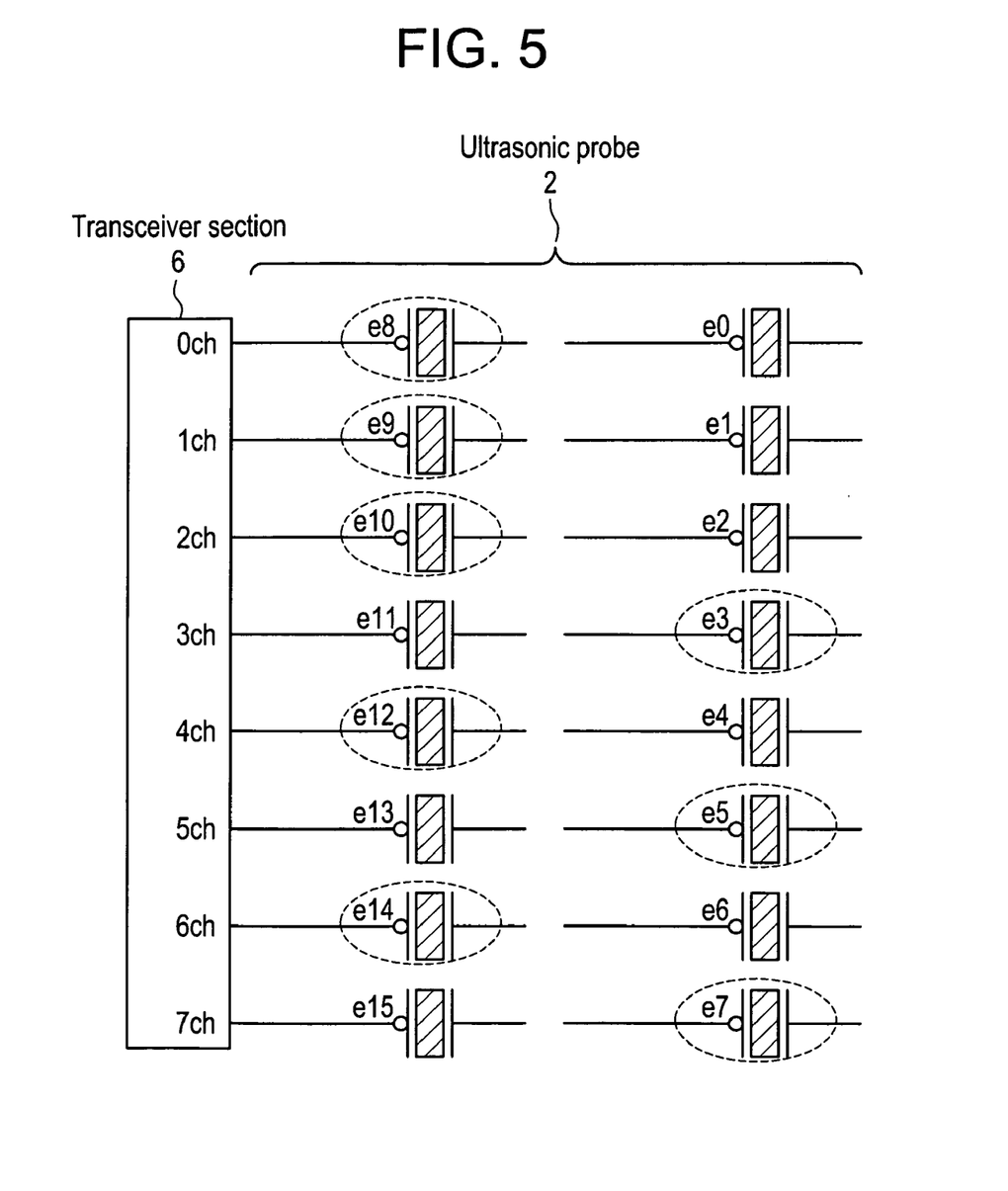
FIG. 5 is a schematic diagram generally showing connection between a transceiver section and transducers in the ultrasonic diagnostic apparatus 1 shown in FIG. 1.

FIG. 5 is a schematic diagram showing correspondence between channels and elements in the first transmission/reception shown in FIG. 4. The high-voltage switches 5 are omitted in the drawing.

As shown in FIG. 5, a channel provided in the transceiver section 6 can turn on one of two elements. An element e that is driven in the first transmission/reception, i.e., an element e connected to a channel via a high-voltage switch 5, is indicated by a surrounding dashed line.

Figure 6:
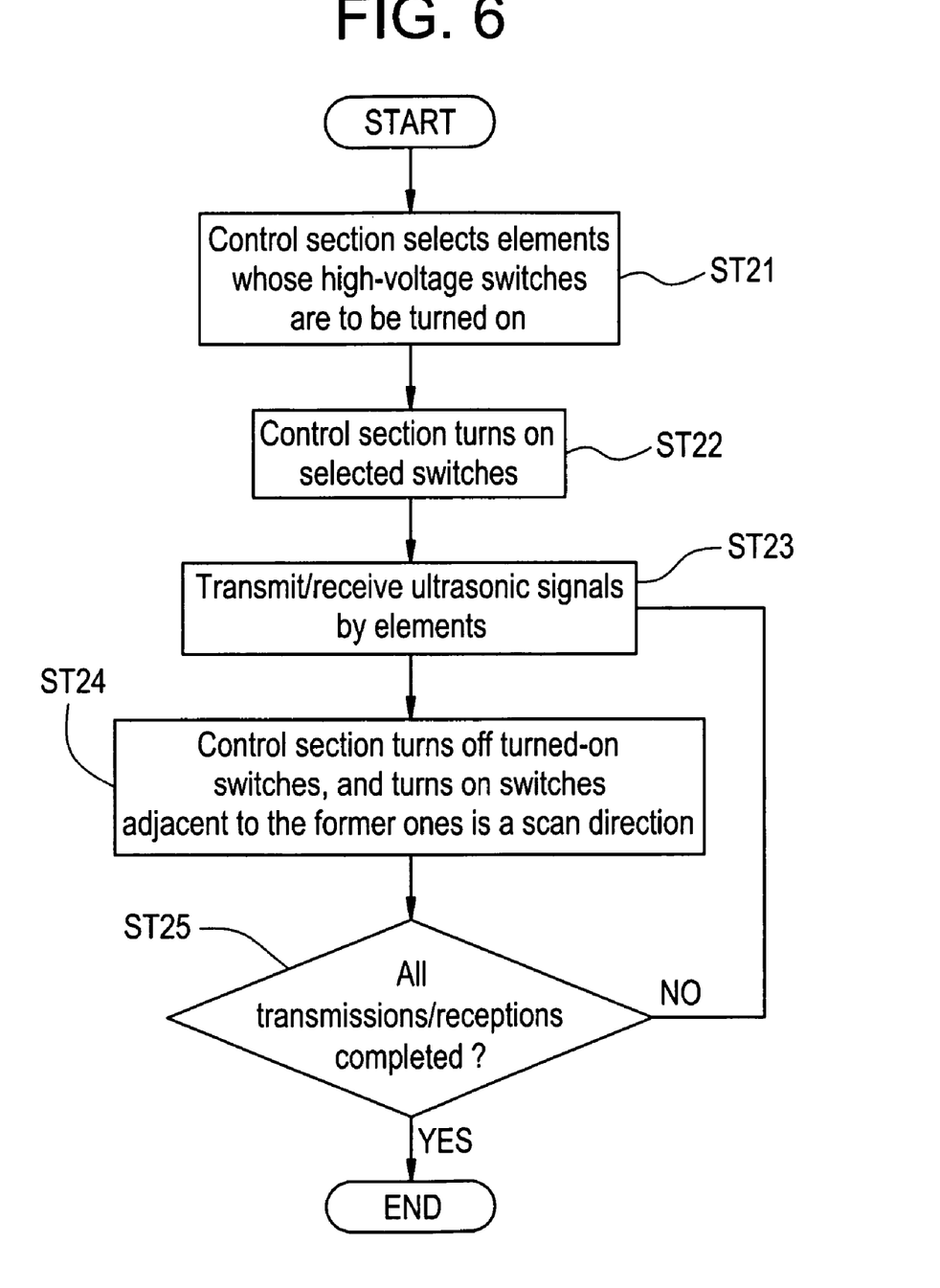
FIG. 6 is a flow chart for explaining a step of defining connection between the transceiver section and transducers in the ultrasonic diagnostic apparatus 1 shown in FIG. 1.

FIG. 6 is a flow chart showing part of the elements selecting step.

The control section 9 first selects elements whose high-voltage switches 5 are to be turned on in the first transmission/reception as shown in FIG. 4 so that the elements are arranged inconsecutively with respect to the arrangement direction (ST21).

As shown in FIGS. 4 and 5, for example, third and fifth elements e3 and e5 are selected to be connected to third and fifth channels, while a fourth element e4 is not selected for preventing it from being driven consecutively with respect to the third and fifth elements e3 and e5. The fourth channel is set to be connected with a twelfth element e12 as shown in FIG. 5.

Moreover, the control section 9 selects high-voltage switches 5 so that the channels are connected with adjoining elements e7–e10 around eighth and ninth elements e8 and e9 that correspond to the central portion of an aperture area from one end to the other of the elements that are connected to the channels, i.e., from third element e3 to fourteenth element e14 in the first transmission/reception, as shown in FIG. 4. On the other hand, the control section 9 selects high-voltage switches 5 so that adjoining elements will not be connected to the channels near the edges of the aperture area.

Once the connection pattern has been established by the control section 9 as described above, the control section 9 turns on the high-voltage switches 5 based on the connection pattern (ST22).

As a result, the channels output ultrasonic signals from the transceiver section 6 to respective elements in the ultrasonic probe 2.

The elements supplied with the output ultrasonic signals transmit them to the subject, and receive reflected waves from the subject (ST23). The received ultrasonic signals are stored in the storage section 8 via the image processing section 7, for example.

Next, a second transmission/reception is conducted.

After the first transmission/reception has ended, the control section 9 turns off the turned-on high-voltage switches, and further, turns on high-voltage switches corresponding to adjacent elements in the scan direction (ST24).

For example, as shown in FIG. 4, the control section 9 turns on high-voltage switches 5 corresponding to second, fourth, sixth–ninth, eleventh and thirteenth elements e2, e4, e6–e9, e11, and e13 that are adjacent in the scan direction to the third, fifth, seventh–tenth, twelfth and fourteenth elements e3, e5, e7–e10, e12 and e14 that were connected to the high-voltage switches 5 in the first transmission/reception.

By repeating similar steps, the ultrasonic probe 2 scans the subject while moving the connection pattern one element by one element in the forward direction by the control section 9. After completing a predetermined number of transmissions/receptions, a scan is conducted while maintaining connections or disconnections between the elements and channels without moving the connection pattern in the scan direction by the control section 9. It should be noted that the control section 9 may move the connection pattern in the scan direction without maintaining the connection pattern. This step is executed until an n-th transmission/reception has been completed, where n is a predetermined number (ST25).

Figure 7:
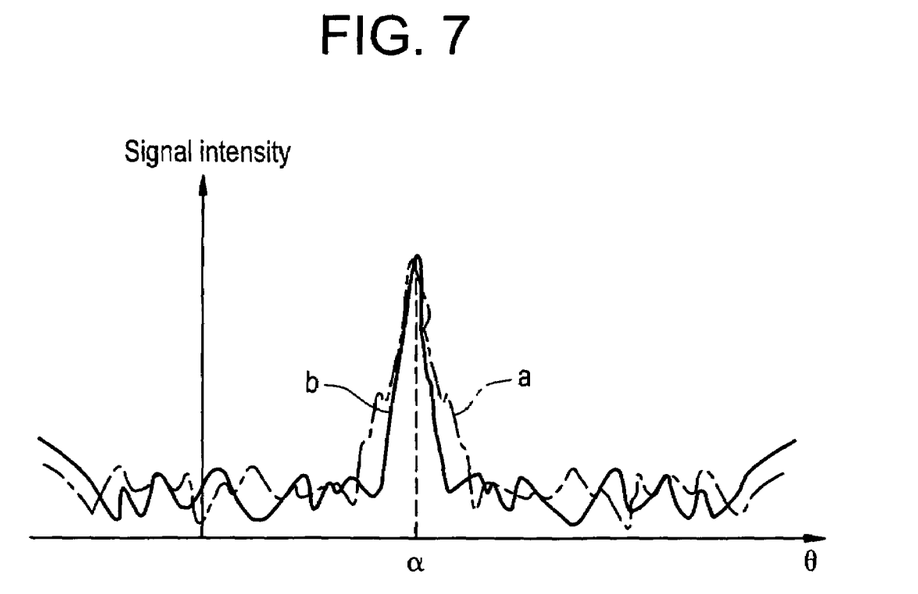
FIG. 7 is a graph showing the relationship between an emission angle and signal intensity obtained by the ultrasonic diagnostic apparatus 1 shown in FIG. 1.

FIG. 7 is a graph showing the relationship between the azimuthal angle for emission of ultrasonic signals and signal intensity. FIG. 7 shows a first ultrasonic signal a by transmission/reception with adjoining elements in the ultrasonic probe consecutively connected to the channels, and a second ultrasonic signal b by transmission/reception using the connection pattern of the present embodiment.

As shown in FIG. 7, the first ultrasonic signal a has a peak width indicating signal intensity that is broadened with respect to a certain emission angle α, whereas the second ultrasonic signal b in accordance with the present embodiment has a peak that is not broadened by widening the aperture area of the elements, and it can be seen that resolution is improved.

(Variation)

A variation of the present embodiment will next be described with reference to the drawings. Similar parts to those in the embodiment above are designated by similar reference numerals, and explanation thereof will be omitted.

Figure 8:
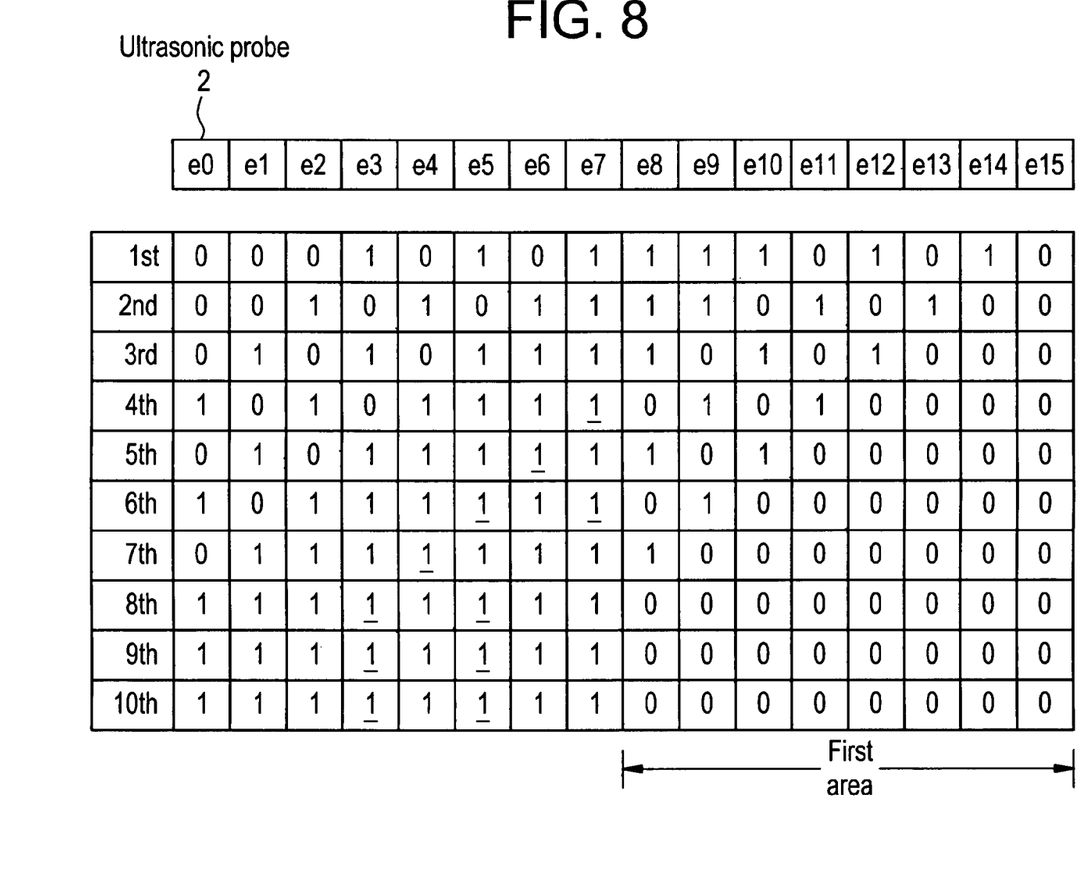
FIG. 8 is a schematic diagram showing another example of the connection pattern of variation 1 in accordance with the present invention.

FIG. 8 shows an example of a successive pattern in accordance with the present variation.

In FIG. 8, part of zeroth–fifteenth elements e1–e15 are connected to channels in the transceiver section 6 as in FIG. 4, and a scan is conducted while moving the successive pattern in a direction from fifteenth element e15 to zeroth element e0 in first–tenth transmissions/receptions.

The first–fourth transmissions/receptions in FIG. 8 are the same as those in FIG. 4.

In the fifth transmission/reception in FIG. 8, the center of the aperture area lies between fourth element e4 and fifth element e5.

Moreover, since the number of channels in the transceiver section 6 in the ultrasonic diagnostic apparatus in accordance with the present embodiment is eight, a first area in which transducers in the same number as the number of channels are arranged in the scan direction corresponds to eighth element e8 through fifteenth element e15.

According to the present variation, the control section 9 connects the channels with all the elements in a region embraced by the center of the aperture area and the edge of the first area near the center of the aperture area.

For example, in the fifth transmission/reception, the center of the aperture area lies between fourth and fifth elements, as shown in FIG. 8. At that time, the control section 9 selects a region embraced by the center of the aperture area and the edge of the first area, i.e., all elements from the fifth through seventh, to be connected to the channels.

Figure 9:
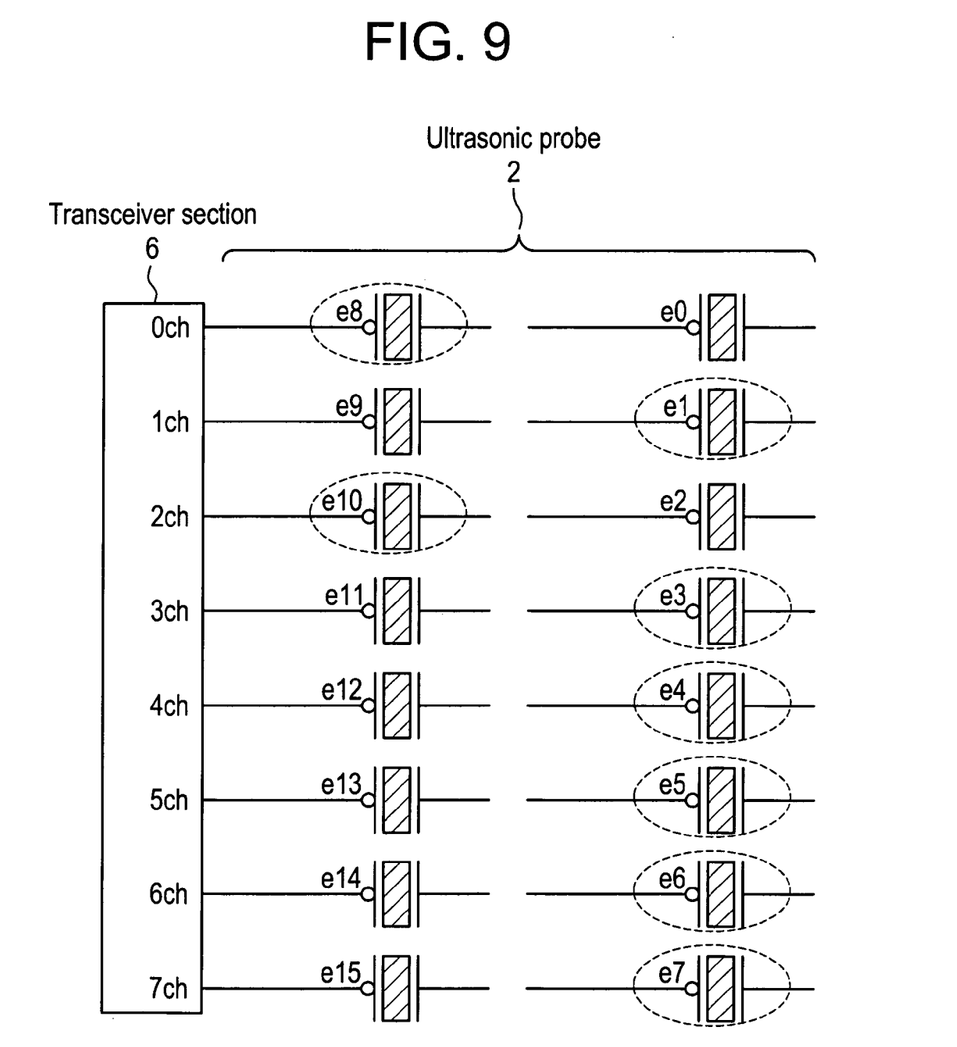
FIG. 9 is a schematic diagram generally showing connection between the transceiver section and transducers in the ultrasonic diagnostic apparatus 1 shown in FIG. 1.

FIG. 9 is a schematic diagram generally showing connections between elements and channels in the fifth transmission/reception.

In the fifth transmission/reception shown in FIG. 4, a seventh channel was not connected to seventh or fifteenth element e7 or e15 connectable to the seventh channel. Thus, in the fifth transmission/reception, elements that conduct transmission/reception are in a number less than the number in the fourth transmission/reception by one.

In the fifth transmission/reception shown in FIG. 9 of the present variation, the control section 9 can maintain a constant number of elements that conduct transmission/reception by turning on a high-voltage switch 5 corresponding to the seventh elements e7.

Similarly, a scan is conducted while moving the connection pattern of the elements and high-voltage switches 5 in the scan direction. After completing a predetermined number of transmissions/receptions, the connection pattern is not moved in the scan direction, and a scan is conducted while maintaining connections or disconnections between the elements and channels. After a predetermined number of transmissions/receptions have been completed, the scan is terminated.

The signal-noise ratio (sometimes referred to as S/N ratio hereinbelow) decreases for a smaller number of channels connected to elements, thus affecting an image to be produced. Since in the present variation, the control section selects elements so that the number of elements connected to channels is kept constant, drop-off of the S/N ratio is reduced.

In the embodiment and variation 1, the ultrasonic probe 2 used is a linear probe or a convex probe.

According to the present embodiment, elements that are driven are distributed widely, and the aperture area is enlarged. As a result, azimuthal sensitivity in transmitting/receiving ultrasonic signals is improved, thus improving resolution. Moreover, since the distribution of the elements that are driven is denser in the center and its vicinity than at the edges and their vicinity of the aperture portion, it is possible to scan a shallower portion. It should be noted that the control section 9 defines a bilaterally symmetric connection pattern with respect to the center of the aperture area for facilitating selection of high-voltage switches.

Furthermore, according to variation 1, since the number of channels is not reduced even if the connection pattern is moved in the scan direction, reduction in the signal-noise ratio can be prevented.

(Second Embodiment)

A second embodiment of the present invention will now be described.

Figure 10:
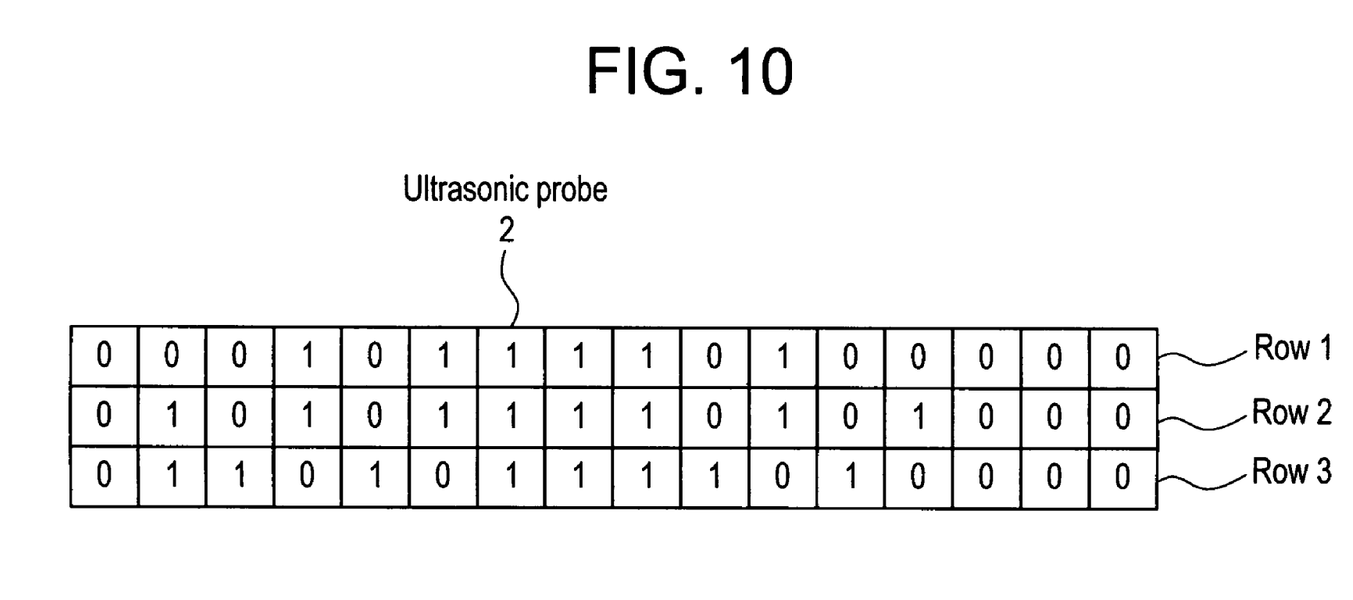
FIG. 10 is a schematic diagram showing an example of a connection pattern in a two-dimensional ultrasonic probe in a second embodiment in accordance with the present invention.

In the present embodiment, the ultrasonic probe 2 used is an AMA probe in which elements are arranged in a two-dimensional manner. Similar parts to those in the embodiment above are designated by similar reference numerals, and explanation thereof will be omitted.

FIG. 10 is a schematic diagram generally showing elements in the AMA probe. While about 128 elements are generally arranged in the longitudinal direction in an AMA probe, the drawing shows 16 elements for simplifying explanation.

Since the AMA probe has elements arranged in a two-dimensional manner, images in two axial directions, i.e., images in longitudinal and transverse directions, can be simultaneously obtained at one observation point.

In an ultrasonic diagnostic apparatus having a smaller number of channels than the number of elements as in the first embodiment, the control section 9 establishes different successive patterns for elements between the rows.

For example, successive patterns for elements in the first–third rows shown in FIG. 10 are different from one another.

Moreover, the control section 9 defines a larger aperture area for the second row that is a central row than the aperture area for the first and third rows.

Furthermore, the number of elements connected to the channels for conducting transmission/reception is six in the first row, whereas the number of elements for conducting transmission/reception is eight in the second row that is a central row. Thus, the control section 9 defines a larger number of elements for conducting transmission/reception in the center than that in the peripheral portion.

According to the present embodiment, in a probe having elements arranged in a two-dimensional manner, elements that are driven are distributed widely, and the aperture area is enlarged. As a result, azimuthal sensitivity in transmitting/receiving ultrasonic signals is improved, thus improving resolution. Moreover, since the distribution of the elements that are driven is denser in the center and its vicinity than at the edges and their vicinity of the aperture portion, it is possible to scan a shallower portion.

The imaging apparatus of the present invention is not limited to the aforementioned embodiments.

For example, in the ultrasonic diagnostic apparatus of the present invention, a convex probe may be used in place of the linear probe. Moreover, the number of the channels in the transceiver section 6 and the number of elements in the ultrasonic probe 2 are illustrated by way of example, and they may be changed as needed.

Besides, several modifications may be made without departing from spirits and scope of the present invention.

Many widely different embodiments of the invention may be configured without departing from the spirit and the scope of the present invention. It should be understood that the present invention is not limited to the specific embodiments described in the specification, except as defined in the appended claims.

The invention claimed is:

1. An ultrasonic diagnostic apparatus for transmitting ultrasonic signals toward a subject, receiving signals reflected from said subject in response to the transmitted ultrasonic signals, and producing a tomographic image of said subject based on the received signals, said apparatus comprising:
   a transmitting/receiving device for transmitting/receiving ultrasonic signals via a plurality of channels; and
   a linear or convex probe in which transducers in a number larger than the number of said channels are arranged in one direction,
   in which probe, said transducers are connected to said channels inconsecutively with respect to the arrangement direction, and the number of said transducers in an aperture area from one end to the other of transducers that are connected to said channels is set to be larger than the number of said channels.

2. The ultrasonic diagnostic apparatus of claim 1, wherein:
   in said probe, said transducers are connected to said channels consecutively in the arrangement direction in the center and its vicinity of said aperture area, and inconsecutively in the arrangement direction at the edges and their vicinity of said aperture area.

3. The ultrasonic diagnostic apparatus of claim 2, wherein:
   in said probe, said transducers are connected to said channels bilaterally symmetrically with respect to the center of said aperture area.

4. The ultrasonic diagnostic apparatus of claim 1, wherein:
   in said probe, when an n-th transducer is connected to one of said channels in an n-th transmission/reception, a transducer adjacent to said n-th transducer in a scan direction is connected to said channel in an (n+1)-th transmission/reception.

5. The ultrasonic diagnostic apparatus of claim 1, wherein:
   in said probe, said aperture area of said probe is moved from one end to the other of said probe in a scan direction during a plurality of transmissions/receptions, and when the center of said aperture area comes nearer to said other end of said probe beyond a first region in which said transducers in a number corresponding to the number of said channels are lined up from said one end of said probe, said transducers lying nearer to said one end from the center of said aperture area except those lying in said first region are connected to said channels.

6. An ultrasonic diagnostic apparatus for transmitting ultrasonic signals toward a subject, receiving signals reflected from said subject in response to the transmitted ultrasonic signals, and producing a tomographic image of said subject based on the received signals, said apparatus comprising:
   a transmitting/receiving device for transmitting/receiving ultrasonic signals via a plurality of channels; and
   a probe in which transducers in a number larger than the number of said channels are arranged in a two-dimensional manner,
   in which probe, said transducers are connected to said channels inconsecutively with respect to one of the arrangement directions so that a connection pattern of said transducers with said channels in each row is different from that in an adjacent transducer row.

7. The ultrasonic diagnostic apparatus of claim 6, wherein:
   in said probe, said transducers are connected to said channels so that the number of the connected transducers is smaller in a peripheral row than in a central row in said probe.

8. The ultrasonic diagnostic apparatus of claim 6, wherein:
   in said probe, an aperture area from one end to the other of transducers that are connected to said channels in the central row in said probe is defined as a larger area than said aperture area in the peripheral row.

9. A driving method for an ultrasonic diagnostic apparatus comprising a transmitting/receiving device for transmitting/receiving ultrasonic signals via a plurality of channels, and a linear or convex probe in which transducers connectable to said channels via switches in a number larger than the number of said channels are arranged in one direction, said method comprising the steps of:
   selecting transducers to be connected to said channels in said transmitting/receiving device, connecting said selected transducers to said channels, transmitting ultrasonic signals toward a subject, and receiving signals reflected in response to the transmitted ultrasonic signals; and
   producing a tomographic image of said subject based on the received signals,
   wherein said transmitting/receiving step comprises selecting said transducers to be connected to said channels inconsecutively in the arrangement direction so that the number of said transducers in an aperture area from one end to the other of transducers that are connected to said channels is larger than the number of said channels.

10. The driving method of claim 9, wherein:
    said transmitting/receiving step comprises selecting said transducers to be connected to said channels consecutively in the arrangement direction in the center and its vicinity of said aperture area, and inconsecutively in the arrangement direction at the edges and their vicinity of said aperture area.

11. The driving method of claim 9, wherein:
    said transmitting/receiving step comprises selecting said transducers so that a connection pattern of said transducers with said channels is bilaterally symmetric with respect to the center of said aperture area.

12. The driving method of claim 9, wherein:
    said transmitting/receiving step comprises, when an n-th transducer is connected to one of said channels in an n-th transmission/reception, selecting a transducer adjacent to said n-th transducer in a scan direction and connecting it to said channel in an (n+1)-th transmission/reception.

13. The driving method of claim 9, wherein:
said transmitting/receiving step comprises conducting transmission/reception while moving said aperture area of said probe from one end to the other of said probe in a scan direction, and when the center of said aperture area comes nearer to said other end of said probe beyond a first region in which said transducers in a number corresponding to the number of said channels are lined up from said one end of said probe, connecting said transducers lying nearer to said one end from the center of said aperture area except those lying in said first region, to said channels.

* * * * *